United States Patent
Noshi et al.

(10) Patent No.: US 8,290,233 B2
(45) Date of Patent: Oct. 16, 2012

(54) X-RAY COMPUTED TOMOGRAPHY APPARATUS AND IMAGE PROCESSING METHOD

(75) Inventors: Yasuhiro Noshi, Otawara (JP); Satoru Nakanishi, Utsunomiya (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 202 days.

(21) Appl. No.: 12/882,876

(22) Filed: Sep. 15, 2010

(65) Prior Publication Data
US 2011/0075905 A1    Mar. 31, 2011

(30) Foreign Application Priority Data
Sep. 29, 2009  (JP) ................................. 2009-225025

(51) Int. Cl.
    *G06K 9/00*  (2006.01)

(52) U.S. Cl. .......................... 382/131; 382/128; 382/154

(58) Field of Classification Search .................. 382/128, 382/131, 154
See application file for complete search history.

(56) References Cited

U.S. PATENT DOCUMENTS

| | | | | |
|---|---|---|---|---|
| 6,631,284 B2 * | 10/2003 | Nutt et al. | ...................... | 600/427 |
| 7,133,041 B2 * | 11/2006 | Kaufman et al. | ............. | 345/419 |
| 7,324,622 B2 | 1/2008 | Morikawa et al. | | |
| 7,428,290 B2 * | 9/2008 | Nishide et al. | ..................... | 378/4 |
| 7,653,229 B2 * | 1/2010 | Kaufhold et al. | ............. | 382/131 |
| 7,773,721 B2 * | 8/2010 | Wu et al. | ......................... | 378/21 |

FOREIGN PATENT DOCUMENTS

| | | |
|---|---|---|
| JP | 2007-275228 | 10/2007 |
| JP | 4056922 | 12/2007 |

* cited by examiner

*Primary Examiner* — Tom Y Lu
(74) *Attorney, Agent, or Firm* — Oblon, Spivak, McClelland, Maier & Neustadt, L.L.P.

(57) ABSTRACT

According to one embodiment, an X-ray computed tomography apparatus includes an X-ray generating unit and an area detector. The reconstruction processing unit reconstructs first and second volume data including an overlap region. The extraction unit extracts first and second slice images from the first and the second volume data respectively. The calculation unit calculates the difference value between a sum of pixel values in the first slice images and the sum of pixel values in the second slice images. The determination unit determines whether the difference value falls within a predetermined range. The combining unit combines the first and second volume data and sets a pixel value in the overlap region to a pixel value of the first volume data, a pixel value of the second volume data, or a value derived from pixel values of the first and second volume data.

17 Claims, 9 Drawing Sheets

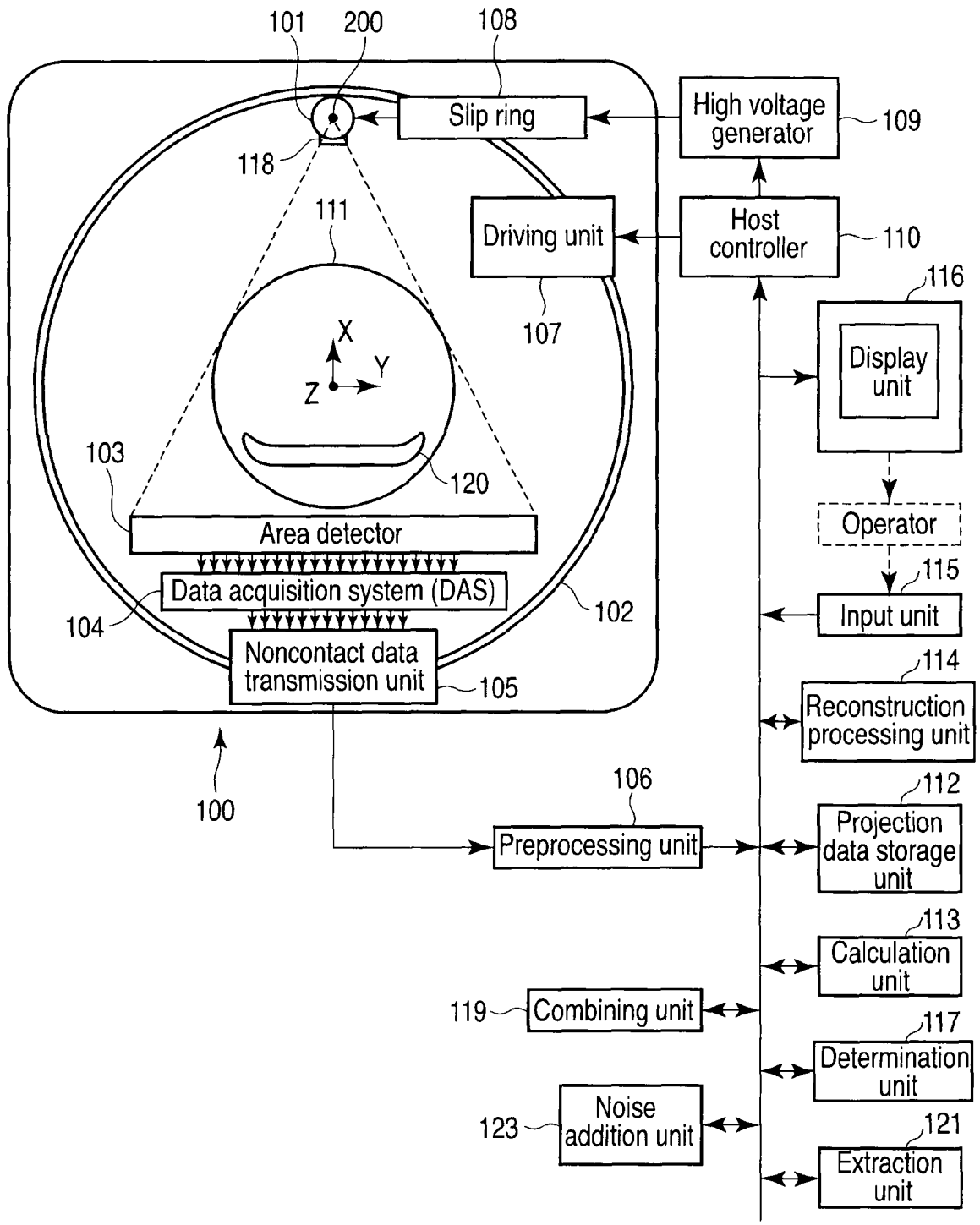
F I G. 1

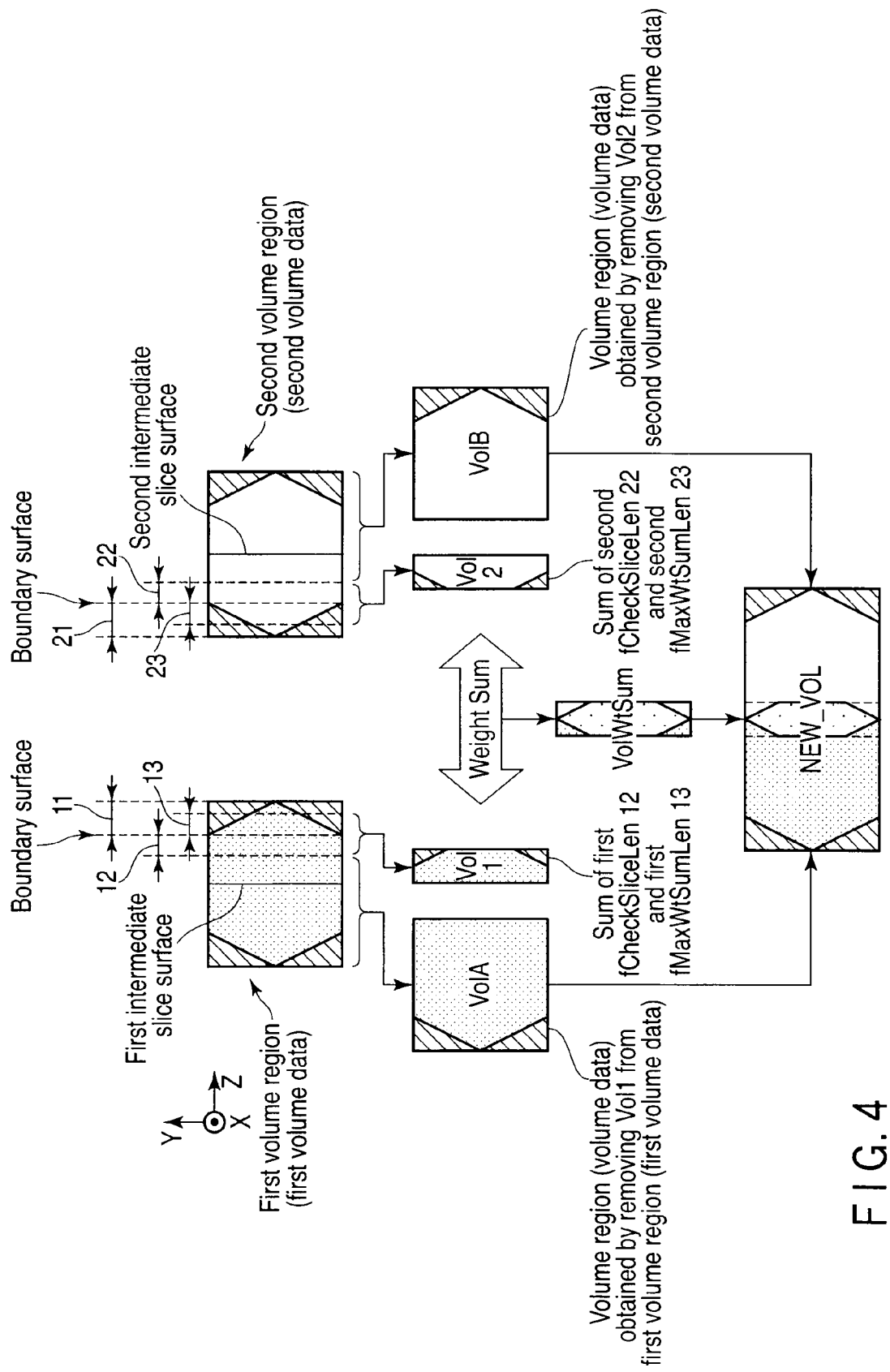
F I G. 4

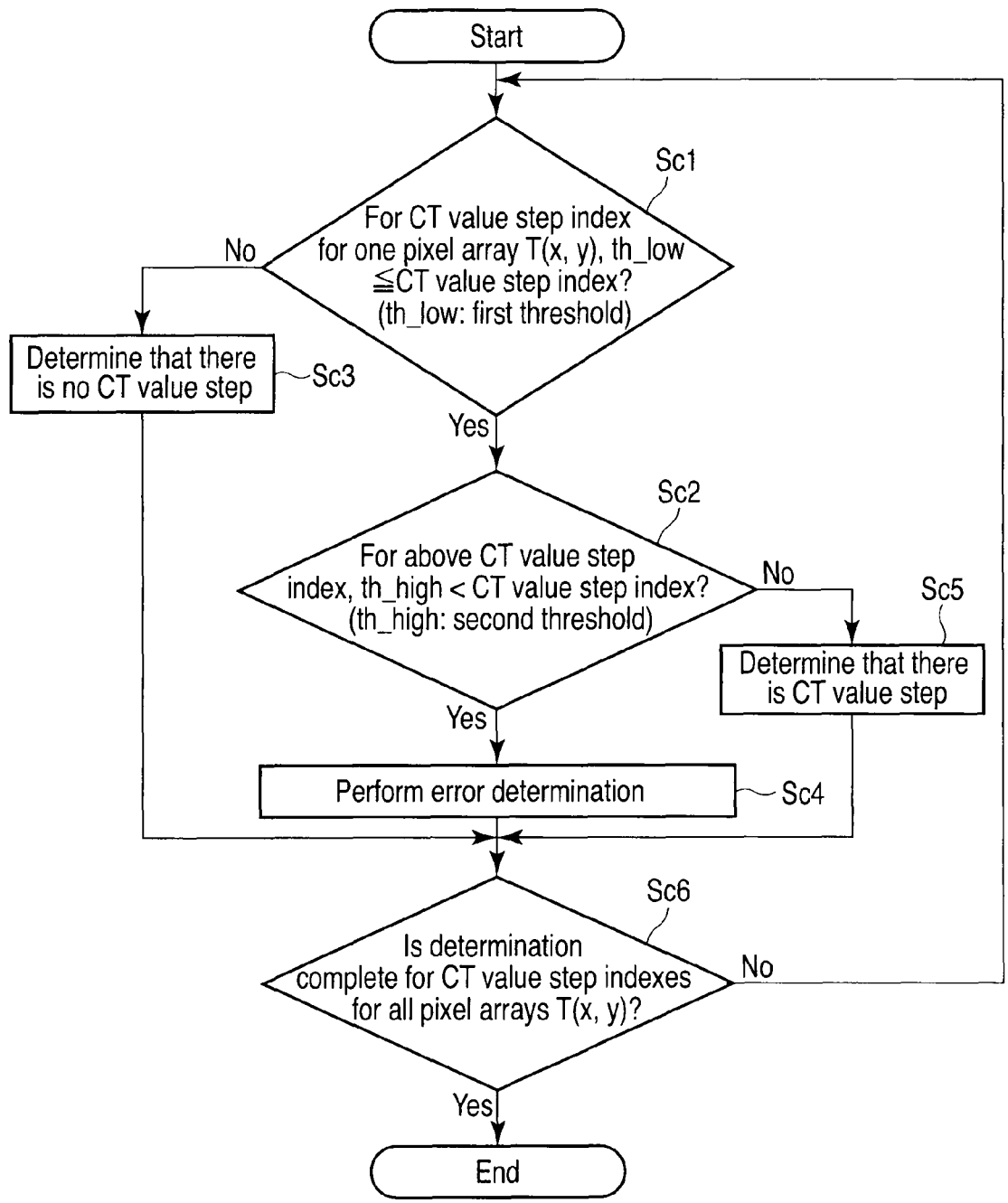
F I G. 6

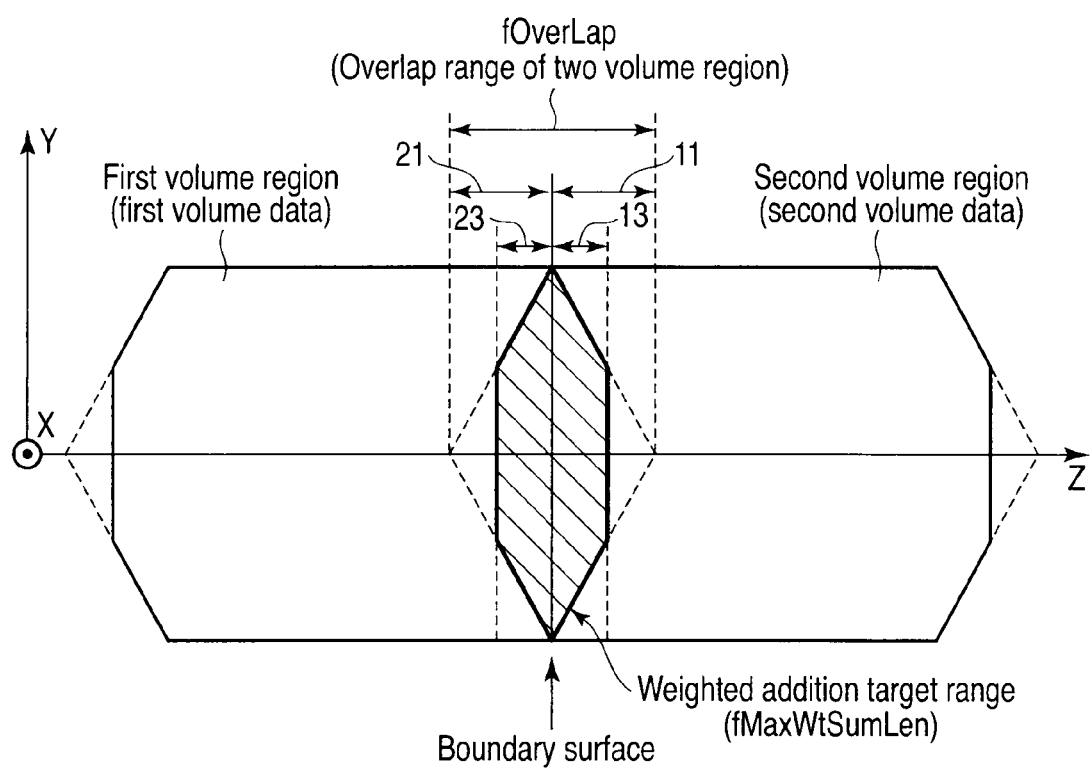
F I G. 8

X-RAY COMPUTED TOMOGRAPHY APPARATUS AND IMAGE PROCESSING METHOD

CROSS-REFERENCE TO RELATED APPLICATIONS

This application is based upon and claims the benefit of priority from Japanese Patent Application No. 2009-225025, filed Sep. 29, 2009; the entire contents of which are incorporated herein by reference.

FIELD

Embodiments described herein relate generally to an X-ray computed tomography apparatus and an image processing method of combining a plurality of volume data.

BACKGROUND

With an increase in the number of X-ray detector arrays, X-ray computed tomography apparatuses tend to frequently use volume data as images to be reconstructed. In order to reconstruct such volume data, projection data corresponding to one rotation around an object, i.e., 360°, is required, or (180°+fan angle) projection data is required in the half scan method. On the boundary between volume data, there are regions having no projection data for reconstruction in a field of view. Each region having no projection data on the boundary between volume data is provided with a mask to cover the region.

There is available a technique of combining and displaying a plurality of volume data along a direction perpendicular to slice surfaces to display a range wider than one volume data.

For example, as a technique to be used when the cone angle of an X-ray cone beam in volume scanning is small, there is available a technique of interpolating pixel values in a region having no volume data by performing weighted addition of a plurality of discrete volume data obtained in advance along a direction perpendicular to slice surfaces and creating a slice image from the interpolated pixel values. This technique interpolates a region having no volume data by an approximate method. In some cases, therefore, a good image cannot be obtained.

Another conventional technique is to, for example, cut the above mask regions near the boundary between two volume data and combine the two cut volume data, thereby combining the two volume data. In this case, simply combining the two volume data may lead to a failure to obtain a good image because of the generation of an apparent boundary (step) between CT values at the joint portion due to the difference in image quality between the two volume data.

BRIEF DESCRIPTION OF THE DRAWINGS

FIG. 1 is a block diagram showing the arrangement of an X-ray computed tomography apparatus according to this embodiment;

FIG. 4 is a view for supplemental explanation of the flowchart of FIG. 3;

FIG. 6 is a flowchart showing a procedure for each process to be executed when a determination unit in this embodiment determines the presence/absence of a CT value step;

FIG. 8 is a view showing the relationship between two volume regions (two volume data) having an overlap region and a weighted addition target range according to this embodiment.

DETAILED DESCRIPTION

Figure 2:
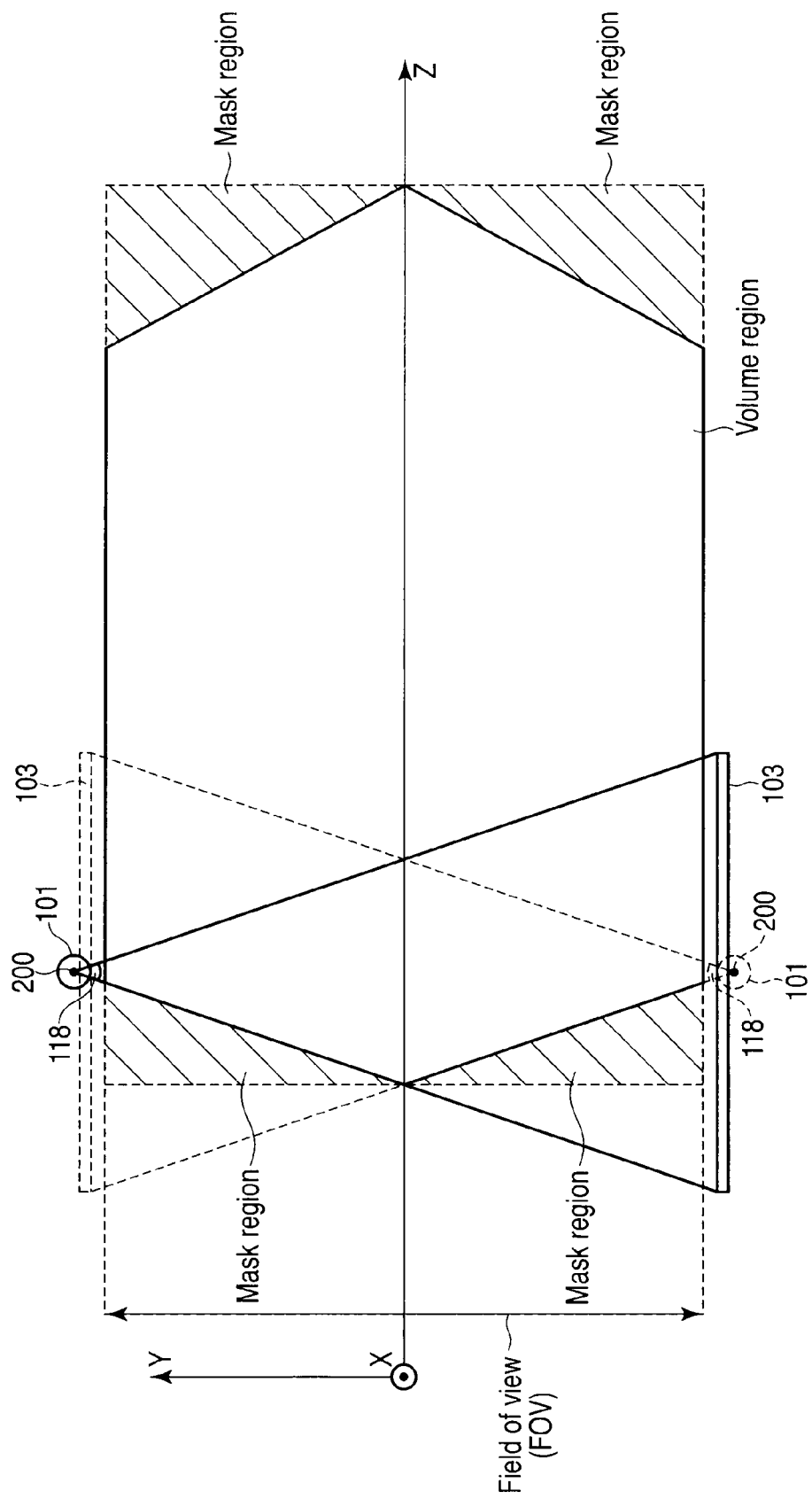
FIG. 2 is a sectional view of a volume region (volume data) in a nearly cylindrical shape on a Y-Z plane according to this embodiment.

In general, according to one embodiment, an X-ray computed tomography apparatus includes an X-ray generating unit, an area detector, a reconstruction processing unit, an extraction unit, a calculation unit, a determination unit, and a combining unit. The X-ray generating unit generates X-rays. The area detector detects X-rays which are generated by the X-ray generating unit and transmitted through an object. The reconstruction processing unit reconstructs the first and second volume data having an overlap region based on an output from the area detector. The extraction unit extracts a plurality of first slice images inside or near the overlap region from the first volume data and extracts a plurality of second slice images inside or near the overlap region from the second volume data. The calculation unit calculates, for each pixel array including the pixel value, the difference value or the absolute value of the difference value between the sum of pixel values along a direction perpendicular to slice surfaces of the plurality of first slice images and the sum of pixel values along the perpendicular direction in the plurality of second slice images. The determination unit determines for each pixel array whether the difference value or the absolute value of the difference value falls within a predetermined range. The combining unit combines the first and second volume data upon position matching and selectively sets the pixel value of each pixel in the overlap region to either one of a pixel value of the first volume data and a pixel value of the second volume data or a value derived from pixel values of the first and second volume data, in accordance with the determination result.

An X-ray computed tomography apparatus according to this embodiment will be described with reference to the views of the accompanying drawing. Note that X-ray computed tomography apparatuses include various types of apparatuses, e.g., a rotate/rotate-type apparatus in which an X-ray generating unit and an X-ray detector rotate together around an object, and a stationary/rotate-type apparatus in which many X-ray detection elements are arrayed in the form of a ring, and only an X-ray generating unit rotates around an object. The embodiment can be applied to either type. In this case, the rotate/rotate type will be exemplified. In order to reconstruct an image, projection data corresponding to one rotation around an object, i.e., 360°, is required, or (180°+fan angle) projection data is required in the half scan method. The embodiment can be applied to either of these reconstruction schemes. The 360° method will be exemplified. As mechanisms of changing incident X-rays into electric charges, the following techniques are the mainstream: an indirect conversion type that converts X-rays into light through a phosphor such as a scintillator and converts the light into electric charges through photoelectric conversion elements such as photodiodes, and a direct conversion type that uses generation of electron-hole pairs in a semiconductor such as selenium by X-rays and migration of the electron-hole pairs to an electrode, i.e., a photoconductive phenomenon. As an X-ray detection element, either of theses schemes can be used. Recently, with advances toward the commercialization of a so-called multi-tube type X-ray computed tomography apparatus having a plurality of pairs of X-ray generating units and X-ray detectors mounted on a rotating ring, related techniques have been developed. The embodiment can be applied to both a conventional single-tube type X-ray computed tomography apparatus and a multi-tube type X-ray computed tomography apparatus. The single-tube type X-ray computed tomography apparatus will be exemplified here.

FIG. 1 is a block diagram showing the arrangement of an X-ray computed tomography apparatus according to this embodiment. A gantry 100 accommodates a rotating support mechanism. The rotating support mechanism includes a rotating ring 102, a ring support mechanism which supports the rotating ring 102 so as to make it rotatable about the rotation axis Z, and a driving unit 107 (electric motor) which rotates and drives the ring. The rotating ring 102 is equipped with an X-ray generating unit 101 and an area detector 103 which is also called a two-dimensional array type or multi-array type detector. The X-ray generating unit 101 receives a voltage and a current from a high voltage generator 109 via a slip ring 108 and emits X-rays from an X-ray focal point 200. A collimator unit 118 attached to the X-ray irradiation window of the X-ray generating unit 101 shapes X-rays emerging from the X-ray focal point 200 into, for example, a cone beam shape (pyramidal shape). The dotted lines indicate the X-ray irradiation range. The X-axis is a straight line which is perpendicular to the rotation axis Z and passes through the focal point 200 of emitted X-rays. The Y-axis is a straight line perpendicular to the X- and Y-axes and the rotation axis Z. For the sake of descriptive convenience, the following description will be made on the assumption that the XYZ coordinate system is a rotating coordinate system which rotates about the rotation axis Z.

The area detector 103 is mounted at a position and angle at which it faces the X-ray generating unit 101 through the rotation axis Z. The area detector 103 includes a plurality of X-ray detection elements. Assume that a single X-ray detection element forms a single channel. A plurality of channels are two-dimensionally arranged in two directions, i.e., the Z direction and the direction of an arc (channel direction) which is perpendicular to the rotation axis Z and whose radius corresponds to the distance from the focal point 200 of X-rays, as a center, from which X-rays emerge, to the center of the light-receiving portion of an X-ray detection element corresponding to one channel. The area detector 103 may be constituted by a plurality of modules each having a plurality of X-ray detection elements arranged in an array. The respective modules are one-dimensionally arranged in nearly the arc direction along the channel direction.

A plurality of X-ray detection elements may be two-dimensionally arranged in two directions, i.e., the channel direction and the slice direction. That is, in the two-dimensional arrangement, a plurality of arrays each having a plurality of channels one-dimensionally arranged along the channel direction are arranged in the slice direction. The area detector 103 having such two-dimensional X-ray detection element arrays may be formed by arranging, in the slice direction, a plurality of arrays each including the plurality of modules one-dimensionally arranged in the nearly arc direction.

When imaging or scanning is to be performed, an object is placed on a top 120 and inserted into a cylindrical imaging area 111 between the X-ray generating unit 101 and the area detector 103. A data acquisition circuit 104, which is called a DAS (Data Acquisition System), is connected to the output of the area detector 103.

The data acquisition circuit 104 is provided with, for each channel, an I-V converter to convert the current signal obtained via each channel of the area detector 103 into a voltage, an integrator to periodically integrate these voltage signals in synchronism with an X-ray irradiation period, an amplifier to amplify an output signal from the integrator, and an analog/digital converter to convert an output signal from the amplifier into a digital signal. The data (pure raw data) output from the data acquisition circuit 104 is transmitted to a preprocessing unit 106 via a noncontact data transmission unit 105 using magnetic transmission/reception or optical transmission/reception.

The preprocessing unit 106 preprocesses the pure raw data output from the data acquisition circuit 104. The preprocessing includes, for example, sensitivity nonuniformity correction processing between channels and the processing of correcting an extreme decrease in signal intensity or signal omission due to an X-ray absorber, mainly a metal portion. The data (called raw data or projection data; projection data in this case) output from the preprocessing unit 106 immediately before reconstruction processing is stored in a projection data storage unit 112 including a magnetic disk, magneto-optical disk, or semiconductor memory in association with data representing view angles at the time of data acquisition.

Note that projection data is a set of data values corresponding to the intensities of X-rays transmitted through an object. For the sake of descriptive convenience, assume that a set of projection data acquired nearly at the same time with one shot at the same view angle throughout all the channels will be referred to as a projection data set. The respective view angles are represented by angles in the range of 0° to 360° which represent the respective positions on a circular orbit centered on the rotation axis Z, along which the X-ray generating unit 101 revolves, with the angle of the uppermost portion on the circular orbit in an upward vertical direction from the rotation axis Z being 0°. Note that projection data of a projection data set which corresponds to each channel is identified by a view angle, cone angle, and channel number.

A reconstruction processing unit 114 has a function of reconstructing three-dimensional images in a nearly cylindrical shape by the Feldkamp method or the cone beam reconstruction method based on a projection data set acquired at view angles in the range of 360° or 180°+fan angle. The reconstruction processing unit 114 generates the first volume data corresponding to a first volume region and generates the second volume data corresponding to a second volume region. The first and second volume region overlaps an overlap region. FIG. 2 is an example of a sectional view of a volume region (volume data) in a nearly cylindrical shape on a Y-Z plane. Regions at the ends of volume data in a direction (Z direction) perpendicular to slice surfaces include regions which lack in 360° projection data required for reconstruction in an imaging field of view 111. A region lacking in projection data is low in reliability of volume data. A region lacking in projection data is not reconstructed or a corresponding reconstructed image is not displayed. This region is generally called a mask region.

The reconstruction processing unit 114 also has a function of reconstructing two-dimensional images (tomographic images) by, for example, the fan beam reconstruction method (also called the fan beam convolution back projection method) or the filtered back projection method. The Feldkamp method is a reconstruction method to be used when projection rays intersect a reconstruction plane like a cone beam. The Feldkamp method is an approximate image reconstruction method of performing processing by regarding a projection beam as a fan projection beam on the premise that the cone angle is small, whereas back projection processing is performed along a ray in scanning operation. The cone beam reconstruction method is a reconstruction method which corrects projection data in accordance with the angle of a ray relative to a reconstruction plane as a method which suppresses cone angle errors more than the Feldkamp method.

An extraction unit 121 extracts a plurality of first slice images inside or near an overlap region, which are used for determination processing (to be described later), from the first volume data. The extraction unit 121 further extracts a plurality of second slice images inside or near an overlap region, which are used for determination processing (to be described later), from the second volume data. A plurality of first slice images used for determination processing (to be described later) are initially set to slices included in the range of a first step determination slice (first fCheckSliceLen) having a predetermined width along a direction perpendicular to a slice surface (boundary surface) that divides an overlap region into two equal regions in, for example, the first volume region (the first volume data), from the boundary surface to a center surface (the first intermediate slice surface) of the first volume region (the first volume data) in the Z direction. The width is set to, for example, 5 mm. However, the user can arbitrarily change the width via an input unit 115. A plurality of second slice images corresponding to the first step determination slice (first fCheckSliceLen) are the second step determination slice (second fCheckSliceLen) having a predetermined width along a direction perpendicular to the boundary surface in the second volume region (the second volume data) from the boundary surface to a center surface (second intermediate slice surface) of the second volume region (the second volume data) in the Z direction. The following description will be made on the assumption that the width of the first step determination slice (first fCheckSliceLen) is equal to that of the second step determination slice (second fCheckSliceLen). In addition, the width of each step determination slice is set to, for example, the value obtained by multiplying the number of slices included in a mask region by a slice width. Note that a processing performed with the extraction unit 121 may be performed by an image generating unit (not shown).

A calculation unit 113 calculates the difference value or the absolute value of the difference value (CT value step index) between the sum or average value of the pixel values (CT values) of pixels included in a pixel array $T(x, y)$ along a direction (Z direction) perpendicular to slice surfaces, with respect to a plurality of first slice images extracted as targets, and the sum or average value of the pixel values (CT values) of pixels included in the pixel array $T(x, y)$ along the Z direction, with respect to a plurality of second slice images extracted as targets, in correspondence with the coordinates of the slice images for each pixel array $T(x, y)$ having these pixels. When calculating average values, the calculation unit 113 excludes the pixel values (CT values) in the mask regions in the above pixel array. Note that a processing performed with the calculation unit 113 may be performed by an two dimensional image processing unit (not shown).

A determination unit 117 determines whether the difference value or the absolute value of the difference value (CT value step index) calculated for each pixel array $T(x, y)$ is included in a predetermined range. The predetermined range is a range which is equal to or more than the first threshold (th_low) and is less than the second threshold (th_high), and is arbitrarily set in accordance with an instruction from the user via the input unit 115. If the CT value step index of the pixel array $T(x, y)$ is less than the first threshold (th_low), the CT value step has no visual influence. If the CT value step index is equal to or more than the second threshold (th_high), the determination unit 117 determines that an abnormality has occurred due to some cause. If the CT value step index is equal to or more than the first threshold (th_low) and is less than the second threshold (th_high), an obvious boundary (step) occurs at the joint portion between the first and second volume data. Note that a processing performed with the determination unit 117 may be performed by an three dimensional image processing unit (not shown).

A combining unit 119 combines the first and second volume region (the first and second volume data) upon position matching. The combining unit 119 selectively sets the pixel value of each pixel in an overlap region to either one of pixel values of the first and second volume data or the value derived from pixel values of the first and second volume data in accordance with the above determination result. Note that in this case, a partial region obtained by omitting the distal ends of an overlap region is a weighted addition target range (fMaxWtSumLen). The combining unit 119 performs the following processing based on the determination result for each pixel in the weighted addition target range (fMaxWtSumLen). Note that a processing performed with the combining unit 119 may be performed by an three dimensional image processing unit (not shown).

The combining unit 119 measures the first distance from a pixel (target pixel), to which attention has been given in the weighted addition target range (fMaxWtSumLen), to the first intermediate slice surface which includes the target pixel and extends along the perpendicular direction (Z direction), when the determination unit 117 determines that there is no CT value step or error. The combining unit 119 further measures the second distance to the second intermediate slice surface which includes the target pixel and extends along the perpendicular direction. The combining unit 119 compares the first and second distances. If second distance<first distance, the combining unit 119 sets, as the pixel value of the target pixel, the pixel value of a pixel in the second volume data which has the same coordinates as those of the target pixel. If second distance first distance, the combining unit 119 sets, as the pixel value of the target pixel, the pixel value of a pixel in the first volume data which has the same coordinates as those of the target pixel.

If the determination unit 117 determines that there is a CT value step, the combining unit 119 performs weighted addition of pixel values of the first and second volume region (the first and second volume data) which overlap by using a predetermined weight generated by the combining unit 119 in the pixel array $T(x, y)$ in the weighted addition target range (fMaxWtSumLen) along the perpendicular direction from the coordinates of the target pixel on a slice surface.

Figure 9:
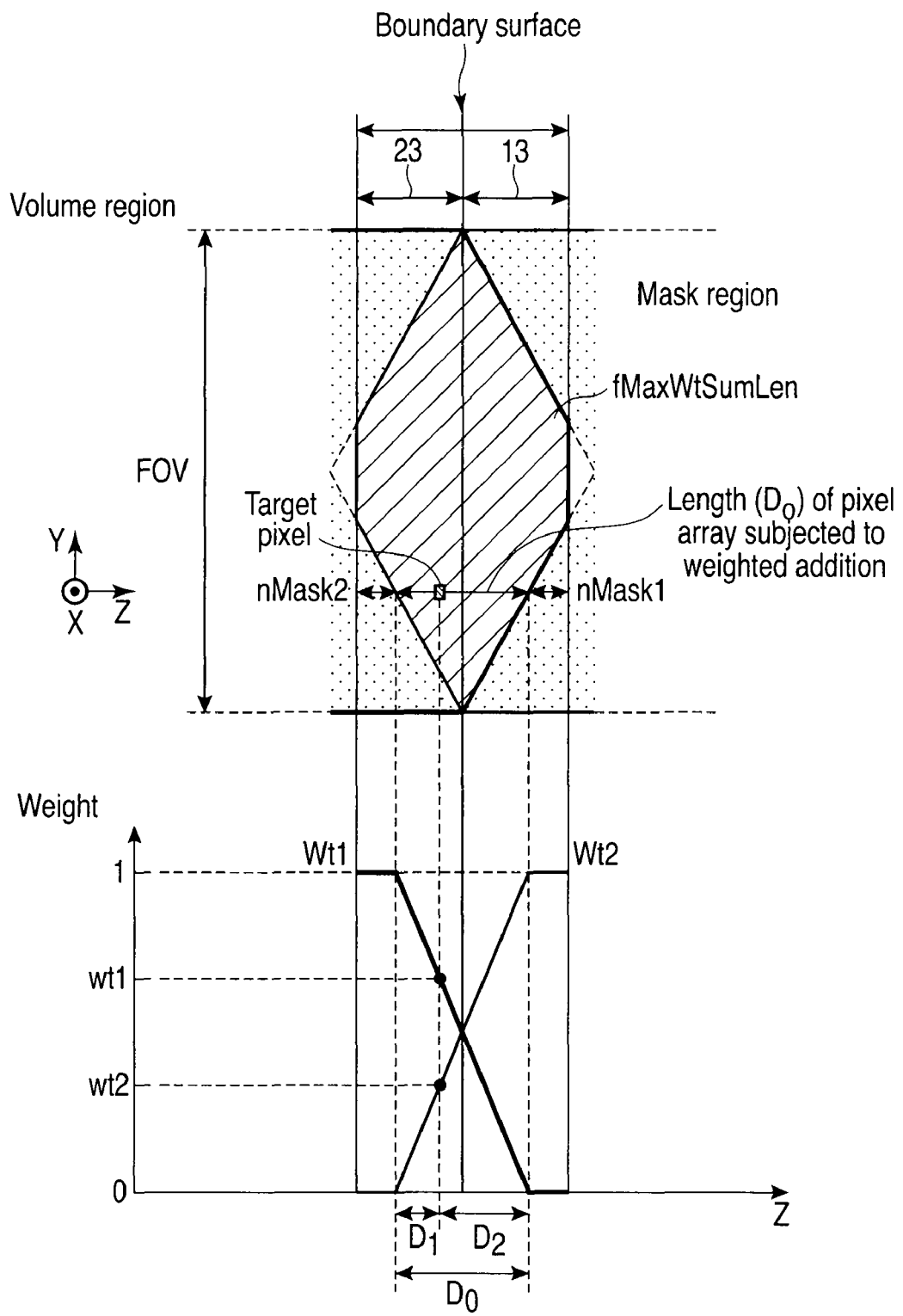
FIG. 9 is a view showing an example of weights for weighted addition according to this embodiment.

The following is an example of the processing of deriving a weight when a predetermined weight generated by the combining unit 119 is a linear weight. First of all, the combining unit 119 measures the length ($D_0$) of the pixel array $T(x, y)$ in the weighted addition target range (fMaxWtSumLen) which includes a target pixel and extends along the perpendicular direction (Z direction). The combining unit 119 then measures the second length ($D_2$) from the target pixel to a boundary of the weighted addition target range (fMaxWtSumLen) extending along the perpendicular direction (Z direction) toward the second intermediate slice surface. The combining unit 119 generates the first weight (Wt1=$D_2/D_0$) to multiply the pixel value of a pixel in the first volume data which has the same coordinates as those of the target pixel, based on the ratio of the second length ($D_2$) to the length ($D_0$) of the pixel array T(x, y). The combining unit 119 measures the first length ($D_1$) from the target pixel to a boundary of the weighted addition target range (fMaxWtSumLen) extending along the perpendicular direction (Z direction) toward the first intermediate slice surface. The combining unit 119 generates the second weight (Wt2=$D_1/D_0$) to multiply the pixel value of a pixel in the second volume data which has the same coordinates as those of the target pixel, based on the ratio of the first length ($D_1$) to the length ($D_0$) of the pixel array T(x, y). The sum of the first and second weights is normalized to 1 (Wt1+Wt2=1). Relational expressions for the respective weights can also be expressed as follows: the first weight (Wt1=($D_0-D_1$)/$D_0$) and the second weight (Wt2=($D_0-D_2$)/$D_0$). FIG. 9 shows these symbols and expressions. This apparatus sets the pixel value of a target pixel by adding the product of the first weight (Wt1) and the pixel value of a pixel in the first volume data which has the same coordinates as those of the target pixel and the product of the second weight (Wt2) and the pixel value of a pixel in the second volume data which has the same coordinates as those of the target pixel. With regard to eight neighboring pixels (adjacent pixels) around a pixel (determination pixel) determined as having a CT value step, the determination result on the central pixel is applied.

The combining unit 119 performs the above processing for the coordinates of each pixel in the weighted addition target range (fMaxWtSumLen). The combining unit 119 generates volume data (third volume data) in the weighted addition target range (fMaxWtSumLen) from the pixel values assigned based on the determined CT value step index and the pixel values obtained by weighted addition. The combining unit 119 generates volume data by combining the volume data in the weighted addition target range (fMaxWtSumLen) generated in the above manner, the first volume data after the extraction of the weighted addition target range (fMaxWtSumLen), and the second volume data after the extraction of the weighted addition target range (fMaxWtSumLen). Note that a plurality of volume data may be combined.

A noise addition unit 123 adds noise to a pixel obtained by weighted addition to prevent the occurrence of high apparent contrast due to signal to noise ratio (SNR) nonuniformity as the noise level of the pixel obtained by weighted addition becomes lower than that of a pixel having undergone no weighted addition. Noise to be added is calculated in the following manner. The noise addition unit 123 measures the standard deviation of noise at neighboring pixels of a pixel obtained by weighted addition. As the neighboring pixels, eight neighboring pixels of the pixel obtained by weighted addition are used. It is possible to obtain the standard deviation of noise to be measured by using the pixel value of the first volume data in the first overlapping volume region and the average value of the CT values derived by the calculation unit 113. It is also possible to calculate the standard deviation of noise to be measured by using the pixel value of the second volume data in the second overlapping volume region and the average value of the CT values derived by the calculation unit 113. Note that noise to be added may be Gaussian noise. It is possible to add noise by using a digital filter. For example, using an enhancement filter will add noise to a pixel obtained by weighted addition by reducing the low-frequency components of the pixel value and enhancing a high-frequency band as the main component of noise.

A display unit 116 displays the images combined by the reconstruction processing unit 114 or the combining unit 119.

Figure 3:
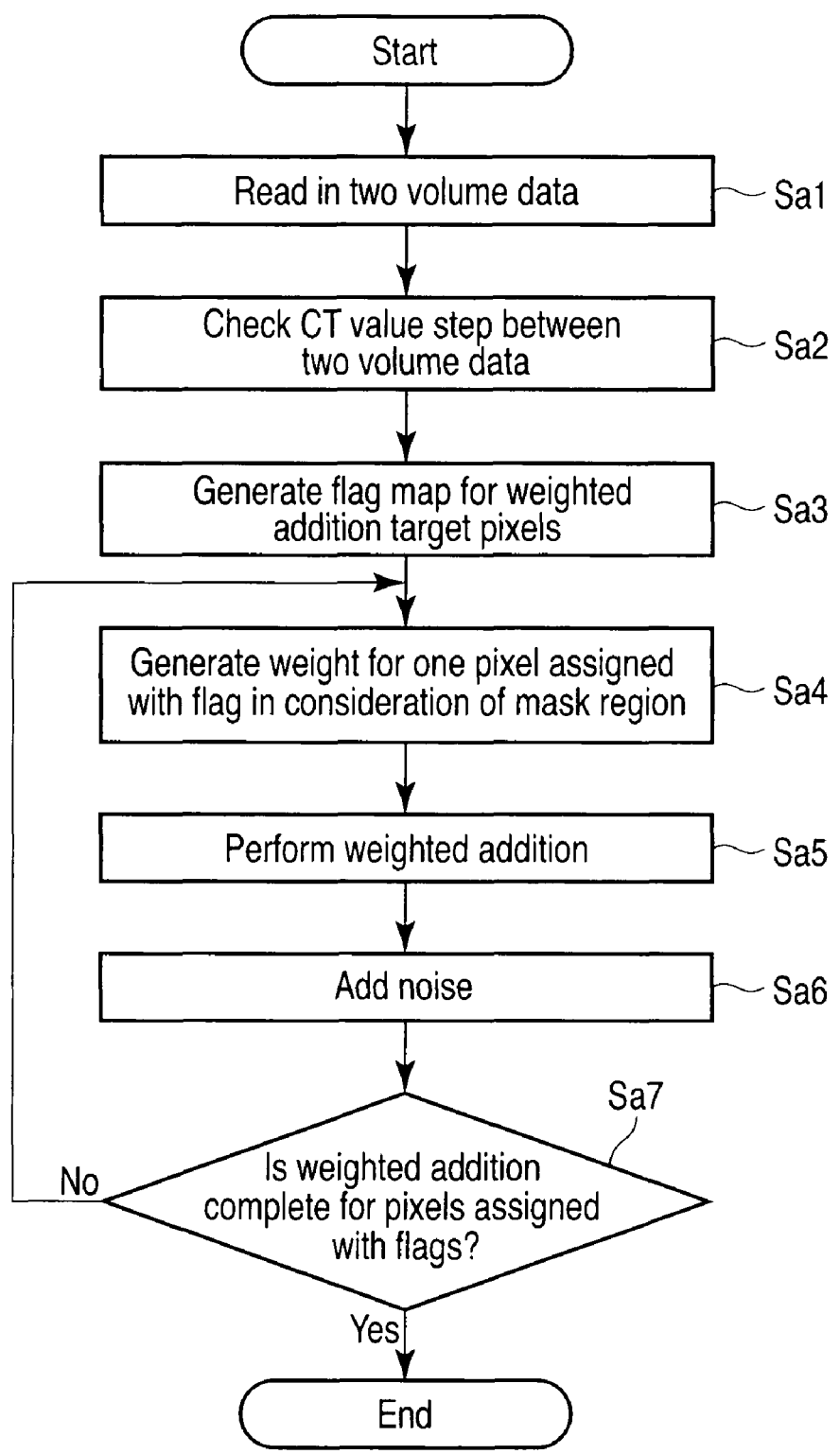
FIG. 3 is a flowchart showing a processing procedure for weighted addition of the pixel values of pixels which overlap according to this embodiment.

FIG. 3 shows an outline of a procedure for a processing method of performing weighted addition in this embodiment. First of all, two volume data to be combined are read in (step Sa1), and a CT value step index between the volume data is derived for each pixel array T(x, y). The determination unit 117 determines, based on the derived CT value step index, the first threshold (th_low), and the second threshold (th_high), whether an obvious boundary (step) occurs at a joint portion between the volume data (step Sa2). The procedure so far is performed by the extraction unit 121, the calculation unit 113, and the determination unit 117, and will be described in detail with reference to FIGS. 5 and 6. The combining unit 119 generates a map indicating whether to perform weighted addition, based on the CT value step index determined for each pixel array T(x, y) (step Sa3). The combining unit 119 sets flags at pixels subjected to weighted addition. The combining unit 119 sets no flags at pixels which are not subjected to weighted addition. The combining unit 119 generates a weight for one of the pixels for which flags are set, in consideration of the number of slices in a mask region (step Sa4). The combining unit 119 performs weighted addition of the respective overlapping pixels by using the generated weight (step Sa5). The noise addition unit 123 adds noise to prevent the occurrence of high apparent contrast due to signal to noise ratio (SNR) nonuniformity as the noise level of the pixel obtained by weighted addition becomes lower than that of a pixel having undergone no weighted addition (step Sa6). After performing noise addition processing (step Sa6), this apparatus repeatedly performs the procedure from generating a weight for one pixel (step Sa4) to adding noise (step Sa6) until the completion of weighted addition processing for all the pixels at which flags are set (step Sa7). The processing in steps Sa3, Sa4, and Sa5 is performed by the combining unit 119 described above, and will be described in detail with reference to FIGS. 7, 8, and 9.

FIG. 4 shows an outline of the processing of performing weighted addition in this embodiment. FIG. 4 is a view for supplemental explanation of the flowchart of FIG. 3. A first overlap (first fOverLap) 11 indicates an overlap region, of the overlapping regions of the first and second volume region (the first and second volume data), which belongs to the first volume region (the first volume data). A second overlap (second fOverLap) 21 indicates an overlap region, of the overlapping regions of the first and second volume region (the first and second volume data), which belongs to the second volume region (the second volume data). A first step determination slice (first fCheckSliceLen) 12 indicates a step determination slice in the first volume region (the first volume data). A second step determination slice (second fCheckSliceLen) 22 indicates a step determination slice in the second volume region (the second volume data). A first weighted addition slice (first fMaxWtSumLen) 13 indicates a weighted addition slice of the first volume region (the first volume data). A second weighted addition slice (second fMaxWtSumLen) 23 indicates a weighted addition slice of the second volume region (the second volume data). An outline of the processing of weighted addition of volume data will be described below. First of all, this apparatus extracts volume data vol1 included in the range of the first step determination slice (first fCheckSliceLen) 12 and first weighted addition slice (first fMaxWtSumLen) 13 from the first volume data. The apparent extracts volume data vol2 included in the range of the second step determination slice (second fCheckSliceLen) 22 and second weighted addition slice (second fMaxWtSumLen) 23 is extracted from the second volume data. The apparatus obtains volume data (VolWtSum) after weighted addition by performing weighted addition (Weight Sum) of each overlapping pixel determined as having a CT value step in the extracted volume data vol1 and vol2. The apparatus then obtains combined volume data (NEW_VOL) by combining volume data volA after the extraction of the volume data vol1 from the first volume data, volume data volB after the extraction of the volume data vol2 from the second volume data, and VolWtSum. FIGS. 3 and 4 show an outline of this embodiment. The flowchart of FIG. 3 and the view of FIG. 4 will be described in detail in association with each process.

Figure 5:
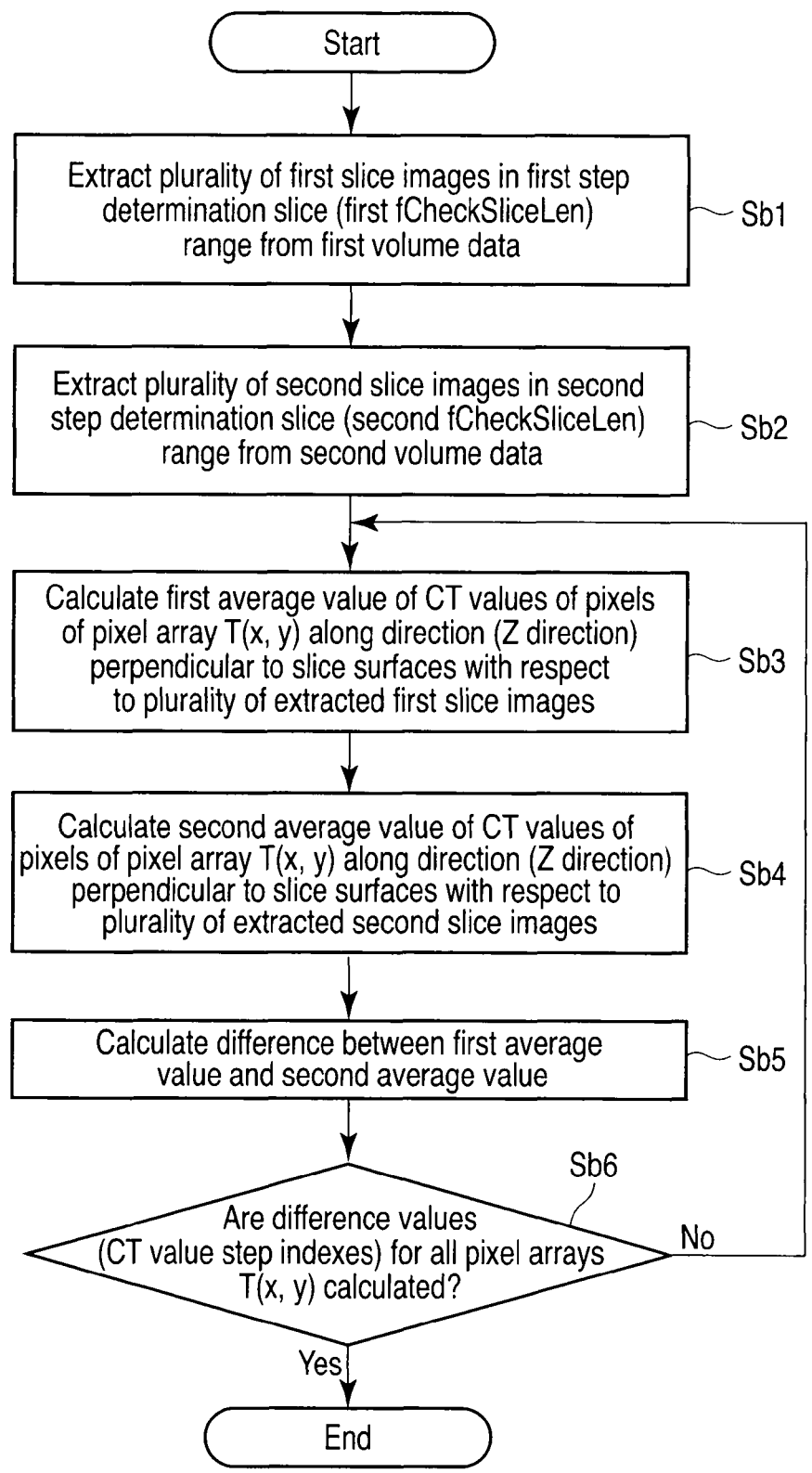
FIG. 5 is a flowchart showing a procedure for each process to be executed when a calculation unit in this embodiment derives a CT value step index.

FIG. 5 shows the details of the procedure for the processing method in steps Sa1 and Sa2 in FIG. 3. The extraction unit 121 and the calculation unit 113 perform processing in accordance with the processing procedure in FIG. 5. First of all, the extraction unit 121 extracts a plurality of first slice images in the range of first step determination slice (first fCheckSliceLen) 12 having a predetermined width from the first volume data (step Sb1). The extraction unit 121 then extracts a plurality of second slice images in the range of second step determination slice (second fCheckSliceLen) 22 having a predetermined width from the second volume data (step Sb2). The calculation unit 113 calculates the first average value or sum of the CT values of pixels included in the pixel array T(x, y) along a direction (Z direction) perpendicular to slice surfaces with respect to the plurality of extracted first slice images as targets (step Sb3). The calculation unit 113 calculates the second average value or sum of the CT values of pixels included in the pixel array T(x, y) along a direction (Z direction) perpendicular to slice surfaces with respect to the plurality of extracted second slice images as targets (step Sb4). The calculation unit 113 calculates the difference between the first average value calculated in step Sb3 and the second average value calculated in step Sb4 (step Sb5). Alternatively, the calculation unit 113 calculates the difference between the first sum calculated in step Sb3 and the second sum calculated in step Sb4. The above difference value will be referred to as a CT value step index hereinafter.

The procedure from the calculation of the first average value or sum (step Sb3) to the calculation of a CT value step index (step Sb5) is performed for each pixel array T(x, y). This apparatus repeatedly performs the procedure from the calculation of the first average value or sum (step Sb3) to the calculation of a CT value step index (step Sb5) until CT value step indexes are calculated throughout all the pixel arrays T(x, y) (step Sb6).

Note that the above CT value step index is calculated by using the first step determination slice (first fCheckSliceLen) 12 and the second step determination slice (second fCheckSliceLen) 22. However, a CT value step index may be calculated by using the first overlap (first fOverLap) 11 and the second overlap (second fOverLap) 21 which are the overlap regions of the respective volume regions (volume data). In addition, a CT value step index may be calculated by using the first weighted addition slice (first fMaxWtSumLen) 13 and second weighted addition slice (second fMaxWtSumLen) 23. Furthermore, it is possible to calculate CT value step indexes by combining these regions. At this time, the CT values of the pixels in the mask regions of a plurality of slice images are excluded.

FIG. 6 shows the details of a procedure for a processing method of determining the presence/absence of a CT value step in step Sa2 in FIG. 3. First of all, if a CT value step index corresponding to one pixel array T(x, y) is less than the first threshold (th_low) (step Sc1), it is determined that there is no CT value step regarding this CT value step index (step Sc3). If the CT value step index is equal to or more than the first threshold (th_low), the CT value step index is sent to the next determination processing (step Sc1). If the sent CT value step index is larger than the second threshold (th_high) (step Sc2), error determination is performed for the CT value step index (step Sc4). If the set CT value step index is equal to or less than the second threshold (th_high) (step Sc2), it is determined that there is a CT value step regarding this CT value step index (step Sc5). This apparatus repeatedly performs the procedure from the determination processing (step Sc1) to the calculation for the determination of the presence of a CT value step (step Sc5) regarding the CT value step indexes for all the pixel arrays T(x, y) until the determination of the presence/absence of a CT value step.

Figure 7:
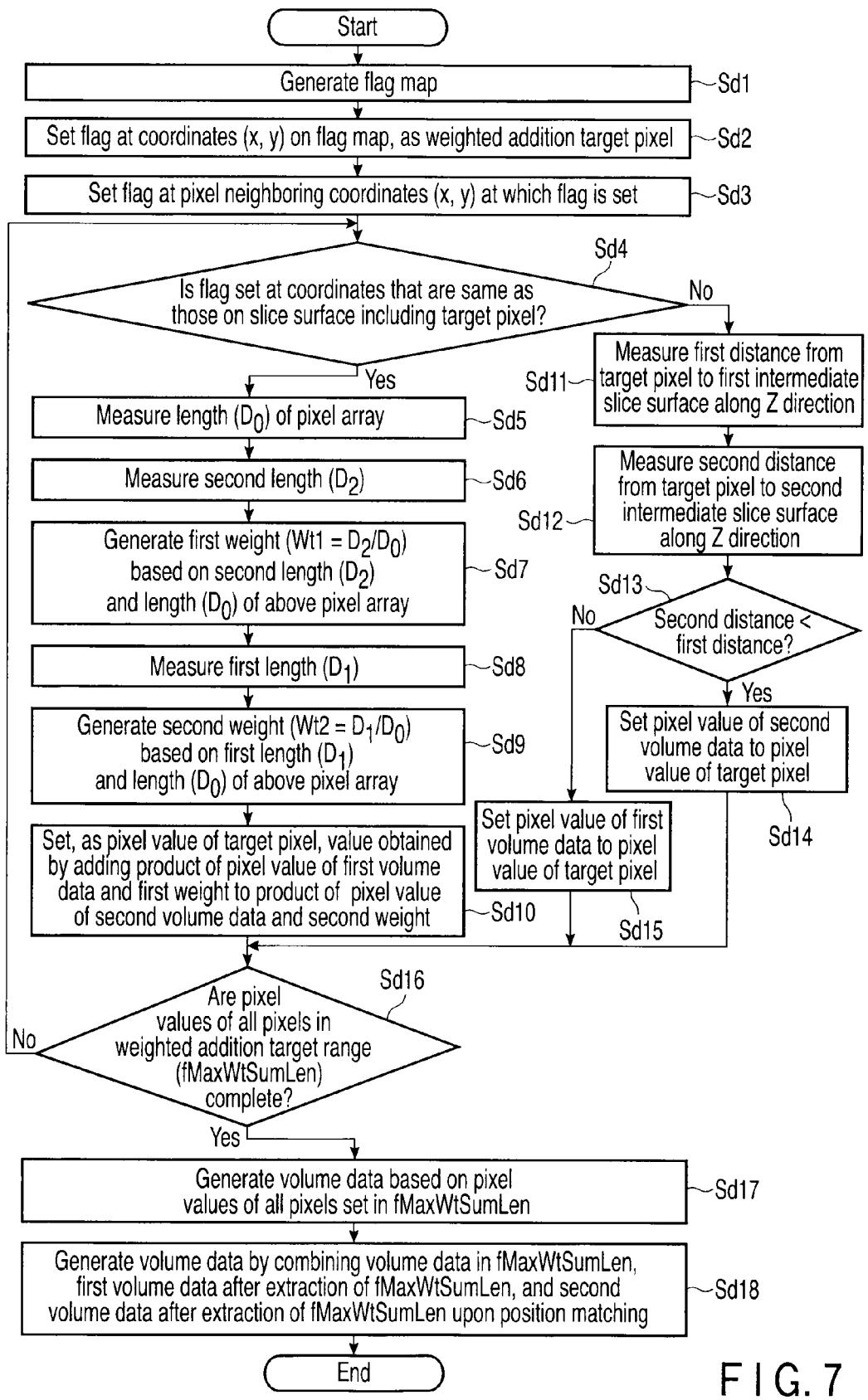
FIG. 7 is a flowchart showing a procedure for each process to be executed when a combining unit in this embodiment generates a flag map, performs weighted addition, and generates a combined image.

FIG. 7 is a flowchart showing an example of a procedure for a processing method in the combining unit 119. Flag map generating processing for a weighted addition target pixel in step Sa3 in FIG. 3 will be described in detail, together with the weighted addition processing in steps Sa4 and Sa5. The generation of weights in weighted addition will be described in detail with reference to FIGS. 8 and 9. Referring back to FIG. 7, this apparatus generates a flag map indicating whether to perform weighted addition (step Sd1). The apparatus sets a flag at coordinates (x, y) on the flag map which are the same coordinates as those of the pixel array T(x, y) determined as having a CT value step by the determination unit 117 (step Sd2). Subsequently, the apparatus sets flags at pixels (to be referred to as neighboring pixels hereinafter) neighboring the coordinates (x, y), at which a flag is set, in accordance with a predetermined rule (step Sd3). In this case, for example, the predetermined rule is that neighboring pixels of the coordinates (x, y), at which a flag is set, are set to (x, y+1) and (x, y−1) on the flag map. Alternatively, the neighboring pixels may be set to (x+1, y+1), (x+1, y−1), (x−1, y+1), and (x−1, y−1). Note that the neighboring pixels may be a matrix of N×M pixels centered on the coordinates (x, y) at which a flag is set. It is also possible to omit steps Sd1 and Sd2.

The combining unit 119 then performs the following processing based on whether a flag is set at the same coordinates on the flag map as those on a slice surface including a pixel (target pixel), in the weighted addition target range (fMaxWtSumLen), to which attention is given (step Sd4). If a flag is set, the combining unit 119 measures the length ($D_0$) of a pixel array between the boundaries of the weighted addition target range (fMaxWtSumLen) which passes through the coordinates of the target pixel and extends along a direction (Z direction) perpendicular to slice surfaces (step Sd5). The length ($D_0$) of the pixel array is, for example, the length of the pixel array along a direction (Z direction) perpendicular to slice surfaces in the weighted addition target range (fMaxWtSumLen) obtained by subtracting mask regions from the sum of the first weighted addition slice (first fMaxWtSumLen) 13 and second weighted addition slice (second fMaxWtSumLen) 23 in FIG. 8.

The combining unit 119 measures the second length ($D_2$) from the target pixel to a boundary of the weighted addition target range (fMaxWtSumLen) along the perpendicular direction (Z direction) toward the second intermediate slice surface (step Sd6). The combining unit 119 generates the first weight ($Wt1=D_2/D_0$) to multiply the pixel value having the same coordinates as those of the target pixel in the first volume data, based on the ratio of the second length ($D_2$) to the length ($D_0$) of the pixel array (step Sd7). The combining unit 119 measures the first length ($D_1$) from the target pixel to a boundary of the weighted addition target range (fMaxWt- SumLen) along the perpendicular direction (Z direction) toward the first intermediate slice surface (step Sd8). The combining unit 119 generates the second weight (Wt2=$D_1$/$D_0$) to multiply a pixel value having the same coordinates as those of the above pixel in the second volume data based on the ratio of the first length ($D_1$) to the length ($D_0$) of the pixel array (step Sd9). The combining unit 119 sets, as the pixel value of the target pixel, the sum (weighted sum) of the product of the pixel value of the first volume data which has the same coordinates as those of the target pixel and the first weight (Wt1) and the product of the pixel value of the second volume data which has the same coordinates as those of the target pixel and the second weight (Wt2) (step Sd10).

If no flag is set, the combining unit 119 measures the first distance from the target pixel to the first intermediate slice surface along the perpendicular direction (Z direction) (step Sd11). Subsequently, the combining unit 119 measure the second distance from the target pixel to the second intermediate slice surface along the perpendicular direction (Z direction) (step Sd12). The combining unit 119 compares the first distance with the second distance (step Sd13). If second distance<first distance, the combining unit 119 sets, as the pixel value of the target pixel, the pixel value of a pixel of the second volume data which has the same coordinates as those of the target pixel (step Sd14). If second distance first distance, the combining unit 119 sets, as the pixel value of the target pixel, the pixel value of a pixel of the first volume data which has the same coordinates as those of the target pixel (step Sd15). The combining unit 119 repeatedly performs the steps from the step of determining whether a flag is set at coordinates on the flag map which are the same as those on the slice surface including the target pixel (step Sd4) to the step of setting, as the pixel value of the target pixel, the pixel value of a pixel of the first data volume which has the same coordinates as those of the target pixel (step Sd15), until setting of pixel values obtained by the above weighted addition, setting of pixel values from the first volume data, or setting of pixel values from the second volume data is complete for the pixel values of all the pixels in the weighted addition target range (fMaxWtSumLen) (step Sd16).

The combining unit 119 then generates volume data in the weighted addition target range (fMaxWtSumLen) from the pixel values of all the pixels set in the weighted addition target range (fMaxWtSumLen) (step Sd17). The combining unit 119 generates volume data by combining the generated volume data in the weighted addition target range (fMaxWtSumLen), the first volume data after the extraction of the weighted addition target range (fMaxWtSumLen), and the second volume data after the extraction of the weighted addition target range (fMaxWtSumLen) upon position matching (step Sd18).

FIG. 8 is a view showing the relationship between two volume regions having an overlap region and a weighted addition target range (fMaxWtSumLen). Reference symbol fOverLap denotes the sum of the first overlap (first fOverLap) 11 and the second overlap (second fOverLap) 21, i.e., the range in which the two volume regions overlap. The weighted addition target range (fMaxWtSumLen) is the region obtained by subtracting the mask regions from the sum of the first weighted addition slice (first fMaxWtSumLen) 13 and the second weighted addition slice (second fMaxWtSumLen) 23. The weighted addition target range (fMaxWtSumLen) is the range in which weighted addition is performed, and is indicated by the hatching. Although FIG. 8 shows the weighted addition target range (fMaxWtSumLen) for the two volume data having the mask regions, it is possible to use volume data having no mask regions.

FIG. 9 shows the relationship between the range in which weighted addition is performed and weights to multiply pixel values of the first and second volume data, as an example of weights for weighted addition. Reference symbol nMask1 denote the value obtained by multiplying the thickness of one slice having mask regions in the first volume region (the first volume data) by the number of slices having mask regions; and nMask2, the value obtained by multiplying the thickness of one slice having mask regions in the second volume region (the second volume data) by the number of slices having mask regions. The FOV (Field Of View) corresponds to the imaging field of view 111.

Reference symbol Weight denotes a weight for the length of the weighted addition target range (fMaxWtSumLen) in the Z direction which is obtained by subtracting the mask regions from the sum of the first weighted addition slice (first fMaxWtSumLen) 13 and the second weighted addition slice (second fMaxWtSumLen) 23. That is, the weighted addition target range (fMaxWtSumLen) is a set of pixel arrays subjected to weighted addition. The length ($D_0$) of a pixel array, in the weighted addition target range (fMaxWtSumLen), which passes through a target pixel and extends along the Z direction, is obtained by subtracting the mask regions (nMask1 and nMask2) from the sum of the first weighted addition slice (first fMaxWtSumLen) 13 and the second weighted addition slice (second fMaxWtSumLen) 23.

Reference symbol Wt1 denotes a weight to multiply a pixel value of the first volume data; and Wt2, a weight to multiply a pixel value of the second volume data. The weights Wt1 and Wt2 in the Z direction each are given in a linear form, and correspond to the view of FIG. 8. The half-tone regions indicate that one volume data of the overlapping volume data is a mask region. Weights are assigned at this time such that 0 is assigned to each pixel value of volume data having a mask region, and 1 is assigned to each pixel value of the other volume data. Reference symbol $D_2$ denotes the second length from the target pixel to a boundary of the weighted addition target range (fMaxWtSumLen) extending along the Z direction toward the second intermediate slice surface. This apparatus obtains the first weight (Wt1=$D_2$/$D_0$) to multiply the pixel value of a pixel of the first volume data which has the same coordinates as those of the target pixel, based on the ratio of the second length ($D_2$) to the length ($D_0$) of the pixel array. Reference symbol $D_1$ denotes the first length from the target pixel to a boundary of the weighted addition target range (fMaxWtSumLen) extending along the perpendicular direction (Z direction) toward the first intermediate slice surface. This apparatus obtains the second weight (Wt2=$D_1$/$D_0$) to multiply the pixel value of a pixel of the second volume data which has the same coordinates as those of the target pixel, based on the ratio of the first length ($D_1$) to the length ($D_0$) of the pixel array. The sum of the first and second weights is 1 (Wt1+Wt2=1). The sum of the first length ($D_1$) and the second length ($D_2$) is the length ($D_0$) of the pixel array ($D_1$+$D_2$=$D_0$).

Relational expressions for the respective weights can also be expressed as follows: the first weight (Wt1=($D_0$−$D_1$)/$D_0$) and the second weight (Wt2=($D_0$−$D_2$)/$D_0$). This apparatus sets, as the pixel value of the target pixel, the value (weighted sum) obtained by adding the product of the first weight (Wt1) and the pixel value of the first volume data which has the same coordinates as those of the target pixel and the product of the second weight (Wt2) and the pixel value of the second volume data which has the same coordinates as those of the target pixel. A weighted sum is set for each target pixel.

Note that this embodiment can be applied to a case in which there is an obvious boundary (step) between CT values in volume region (volume data) in the X and Y directions. In this embodiment, the number of volume region (volume data) to be combined is limited to two. However, a plurality of volume region (volume data) may be combined.

The above arrangement can obtain the following effects.

When combining volume regions (volume data) having an overlap region, this X-ray computed tomography apparatus performs weighted addition by using the volume data of at least part of the overlap region which is not used for display. In addition, the apparatus adds noise to each pixel obtained by weighted addition to prevent the occurrence of high apparent contrast due to signal to noise ratio (SNR) nonuniformity as the noise level of the pixel obtained by weighted addition becomes lower than that of each pixel having undergone no weighted addition. This can improve the steps at the joint portion on the boundary between volume regions (volume data). This can also smooth the boundary between the volume regions (volume data) which is noticeable due to a structure which is intermittent in a direction (Z direction) perpendicular to slice surfaces or the difference in image quality between the volume data to be combined. This allows smooth diagnosis. Furthermore, it is possible to trace an internal body structure in an object typified by an organ or blood vessel which is intermittent in the perpendicular direction (Z direction) at the boundary between the volume regions (volume data) across the volume regions (volume data).

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
   an X-ray generating unit configured to generate X-rays;
   an area detector configured to detect X-rays which are generated by the X-ray generating unit and transmitted through an object;
   a reconstruction processing unit configured to reconstruct first volume data and second volume data which include an overlap region, based on an output from the area detector;
   an extraction unit configured to extract a plurality of first slice images inside or near the overlap region from the first volume data and extract a plurality of second slice images inside or near the overlap region from the second volume data;
   a calculation unit configured to calculate, for each pixel array including the pixel value, a difference value or an absolute value of the difference value between a sum of pixel values along a direction perpendicular to slice surfaces of the plurality of first slice images and a sum of pixel values along the perpendicular direction in the plurality of second slice images;
   a determination unit configured to determine for the each pixel array whether the difference value or the absolute value of the difference value falls within a predetermined range; and
   a combining unit configured to combine the first volume data and the second volume data upon position matching and selectively set a pixel value of each pixel in the overlap region to either one of a pixel value of the first volume data and a pixel value of the second volume data or a value derived from pixel values of the first volume data and the second volume data in accordance with the determination result.

2. The apparatus according to claim 1, wherein the derived value is a value obtained by adding a value obtained by multiplying each pixel value of the pixel array in the second volume data by a second weight to a value obtained by multiplying each pixel value of the pixel array in the first volume data by a first weight.

3. The apparatus according to claim 2, wherein the first weight is a value corresponding to a ratio of a length from the pixel to a boundary of the overlap region extending along the perpendicular direction toward a second intermediate slice surface which divides the second volume data into two equal portions to a length of a pixel array along the perpendicular direction in the overlap region, and
   the second weight is a value corresponding to a ratio of a length from the pixel to the boundary extending along the perpendicular direction toward a first intermediate slice surface which divides the first volume data into two equal portions to the length of the pixel array.

4. The apparatus according to claim 1, wherein the calculation unit calculates, for each pixel array including the pixel value, a difference value or an absolute value of a difference value between an average value of pixel values along a direction perpendicular to slice surfaces of the plurality of first slice images and an average value of pixel values along the perpendicular direction in the plurality of second slice images.

5. The apparatus according to claim 3, wherein the combining unit sets a pixel value of a pixel included in the pixel array regarding the determination result that the difference value or the absolute value of the difference value falls without the predetermined range to a pixel value of one of the first volume data or the second volume data which corresponds to a shorter one of distances from the pixel to the first intermediate slice surface and the second intermediate slice surface along the perpendicular direction.

6. The apparatus according to claim 1, wherein the combining unit applies the determination result to an adjacent pixel of the pixel of the pixel array for which it is determined that the difference value or the absolute value of the difference value falls within a predetermined range.

7. The apparatus according to claim 1, further comprising a noise addition unit configured to add noise to the derived value based on noise of an adjacent pixel of the pixel array.

8. The apparatus according to claim 7, wherein the noise addition unit adds noise by using a digital filter.

9. An image processing method comprising:
   extracting, from first volume data, a plurality of first slice images inside or near an overlap region where the first volume data overlaps a second volume data;
   extracting, from the second volume data, a plurality of second slice images inside or near the overlap region;
   calculating, for each pixel array including the pixel value, a difference value or an absolute value of a difference value between a sum of pixel values along a direction perpendicular to slice surfaces of the plurality of first slice images and a sum of pixel values along the perpendicular direction in the plurality of second slice images;
   determining, for the each pixel array, whether one of the calculated difference value and the absolute value of the difference value falls within a predetermined range;
   selectively setting a pixel value of each pixel in the overlap region to either one of a pixel value of the first volume data and a pixel value of the second volume data or a value derived from pixel values of the first volume data and the second volume data, in accordance with the determination result; and combining the first volume data and the second volume data upon position matching by using the set pixel value.

10. The method according to claim 9, wherein a value obtained by adding a value obtained by multiplying each pixel value of the pixel array in the second volume data by a second weight to a value obtained by multiplying each pixel value of the pixel array in the first volume data by a first weight is generated as the derived value.

11. The method according to claim 10, wherein a value corresponding to a ratio of a length from the pixel to a boundary of the overlap region extending along the perpendicular direction toward a second intermediate slice surface which divides the second volume data into two equal portions to a length of a pixel array along the perpendicular direction in the overlap region is generated as the first weight, and a value corresponding to a ratio of a length from the pixel to the boundary extending along the perpendicular direction toward a first intermediate slice surface which divides the first volume data into two equal portions to the length of the pixel array is generated as the second weight.

12. The method according to claim 9, wherein a difference value or an absolute value of a difference value between an average value of pixel values along a direction perpendicular to slice surfaces of the plurality of first slice images and an average value of pixel values along the perpendicular direction in the plurality of second slice images is calculated for each pixel array including the pixel value.

13. The method according to claim 11, wherein a pixel value of a pixel of the pixel array, for which it is determined that the difference value or the absolute value of the difference value does not fall within the predetermined range, is set to a pixel value of one of the first volume data and the second volume data which corresponds to a shorter one of distances from the pixel to the first intermediate slice surface and the second intermediate slice surface along the perpendicular direction.

14. The method according to claim 9, wherein the determination result is applied to an adjacent pixel of the pixel of the pixel array for which it is determined that the difference value or the absolute value of the difference value falls within a predetermined range.

15. The method according to claim 9, wherein noise is added to the derived value based on noise of an adjacent pixel of the pixel array.

16. The method according to claim 9, wherein noise is added by a digital filter based on noise of an adjacent pixel of the pixel array.

17. An X-ray computed tomography apparatus comprising:

an X-ray generating unit configured to generate X-rays;

an area detecting unit configured to detect the X-ray which are generated by the X-ray generating unit and transmitted through an object;

a reconstruction processing unit configured to reconstruct first and second volume data corresponding to first and second volume region respectively, the first volume region being overlapped with the second volume region in an overlap region;

an image generating unit configured to generate a plurality of first slice images corresponding to the overlap region based on the first volume data, generate a plurality of second slice images corresponding to the overlap region based on the second volume data;

a two dimensional image processing unit configured to generate first addition image based on the plurality of first slice images, to generate second addition image based on the plurality of second slice images, and to generate subtraction image based on the first and the second addition image;

a three dimensional image processing unit configured to generate a third volume data corresponding to combination region which is combined by the first and the second volume region based on the first and the second volume data, a pixel in the overlap region includes a pixel value selected from a pixel value of the first volume data, a pixel value of the second volume data and a value derived from a pixel value of the first and the second volume data, in accordance with the pixel in the subtraction image.

* * * * *